(12) United States Patent
Keller

(10) Patent No.: US 7,387,635 B2
(45) Date of Patent: Jun. 17, 2008

(54) SURGICAL INSTRUMENT FOR INSERTING AN INTERVERTEBRAL ENDOPROSTHESIS

(75) Inventor: Arnold Keller, Kayhude (DE)

(73) Assignee: Link Spine Group, Inc., Branford, CT (US)

( * ) Notice: Subject to any disclaimer, the term of this patent is extended or adjusted under 35 U.S.C. 154(b) by 586 days.

(21) Appl. No.: 10/363,164

(22) PCT Filed: Dec. 28, 2001

(86) PCT No.: PCT/EP01/15357

§ 371 (c)(1),
(2), (4) Date: Mar. 5, 2003

(87) PCT Pub. No.: WO02/054994

PCT Pub. Date: Jul. 18, 2002

(65) Prior Publication Data

US 2004/0220582 A1    Nov. 4, 2004

(30) Foreign Application Priority Data

Jan. 12, 2001   (EP) ................. 011007549
Oct. 29, 2001   (EP) ................. 011257920

(51) Int. Cl.
*A61B 17/56* (2006.01)
*A61F 2/46* (2006.01)

(52) U.S. Cl. ........................................................ 606/99
(58) Field of Classification Search .................. 606/86, 606/90, 99, 100, 105, 205, 206, 207, 208
See application file for complete search history.

(56) References Cited

U.S. PATENT DOCUMENTS 3,486,505 A    12/1969  Morrison
5,364,397 A *  11/1994  Hayes et al. .................. 606/61
5,431,658 A     7/1995  Moskovich
6,159,215 A *  12/2000  Urbahns et al. ............... 606/86
6,478,800 B1 * 11/2002  Fraser et al. .................. 606/99

FOREIGN PATENT DOCUMENTS

| DE | 299 16 078 U1 | 12/1999 |
| DE | 200 12 549 U1 | 11/2000 |
| EP | 0 077 159 A1  | 4/1983 |
| EP | 0 333 990 A2  | 9/1989 |
| FR | 2 737 656 A1  | 2/1997 |

* cited by examiner

*Primary Examiner*—Eduardo C. Robert
*Assistant Examiner*—Nicholas Woodall
(74) *Attorney, Agent, or Firm*—Dickstein, Shapiro, LLP.

(57) ABSTRACT

Surgical instrument for inserting an intervertebral endoprosthesis consisting of two prosthesis plates and a prosthesis core. The instrument has two prosthesis holders open at the ends that can be spread apart from each other. In order not to have to remove the instrument from the prosthesis with the latter being under unfavourable loading, it is provided with a withdrawal device which bears on the prosthesis and/or on an associated vertebra. The withdrawal device comprises a slide having a prosthesis limit stop for the prosthesis located in the guide and/or a vertebral limit stop for a vertebra which is to be connected to the prosthesis. The slide is displaceable in a slide guide between a retracted end position and an advanced end position by an actuating device.

14 Claims, 11 Drawing Sheets

Figure 1:
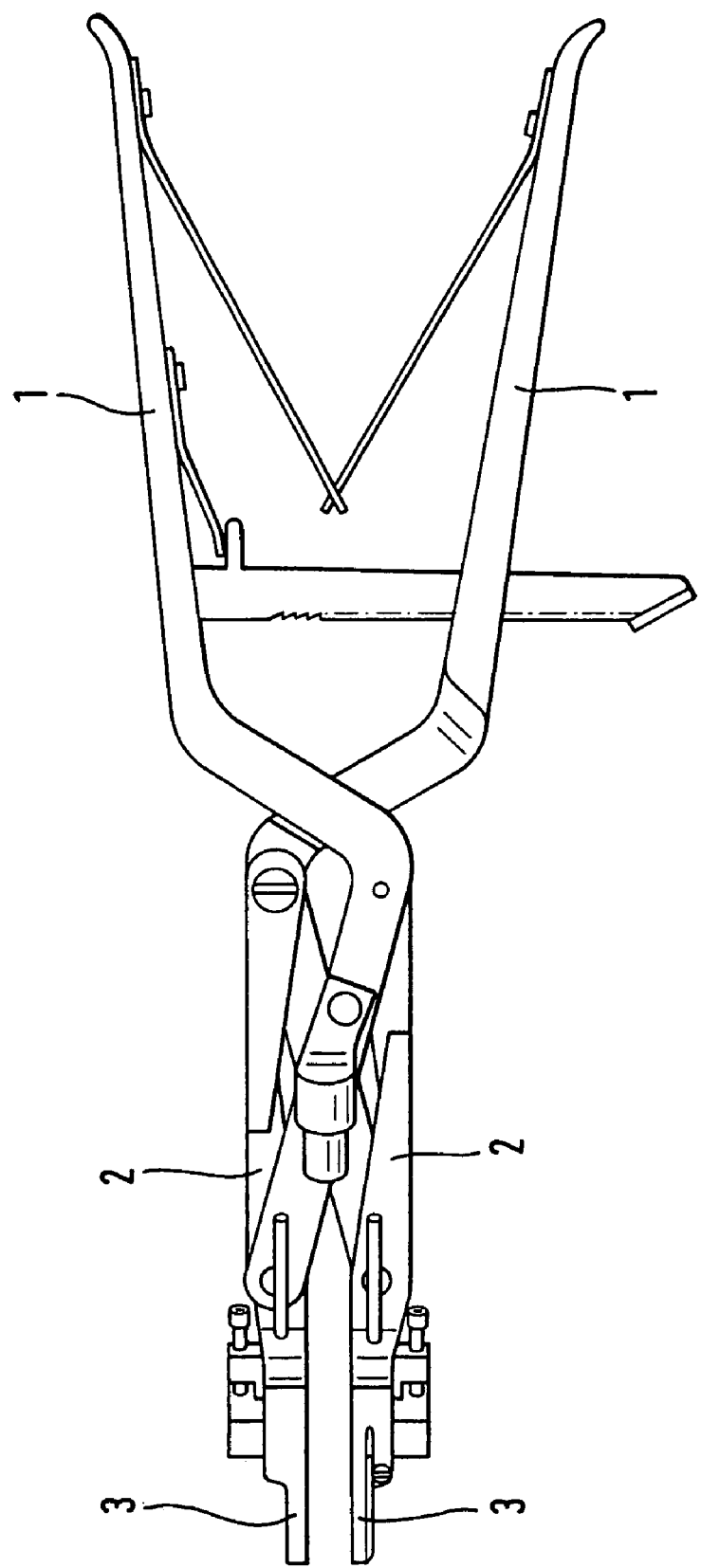

Fig. 6
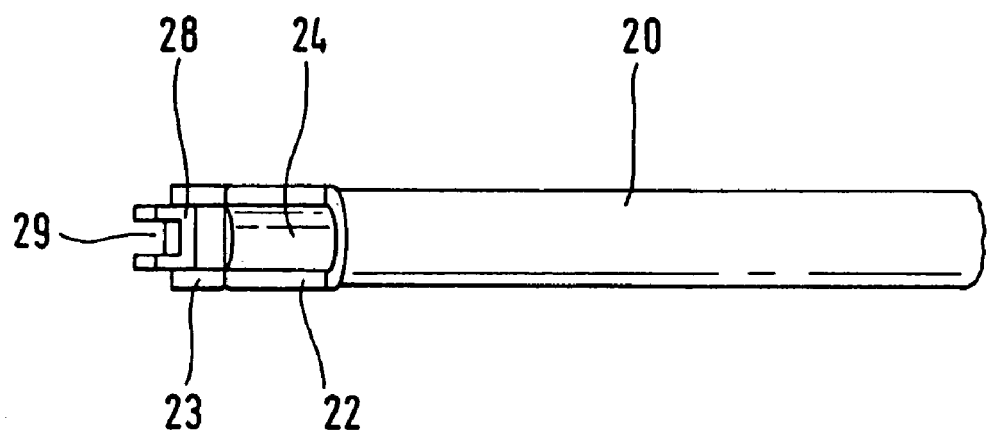
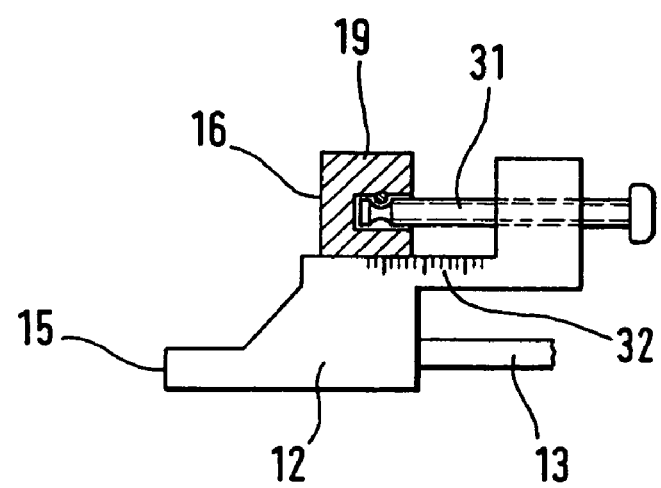
Fig. 7

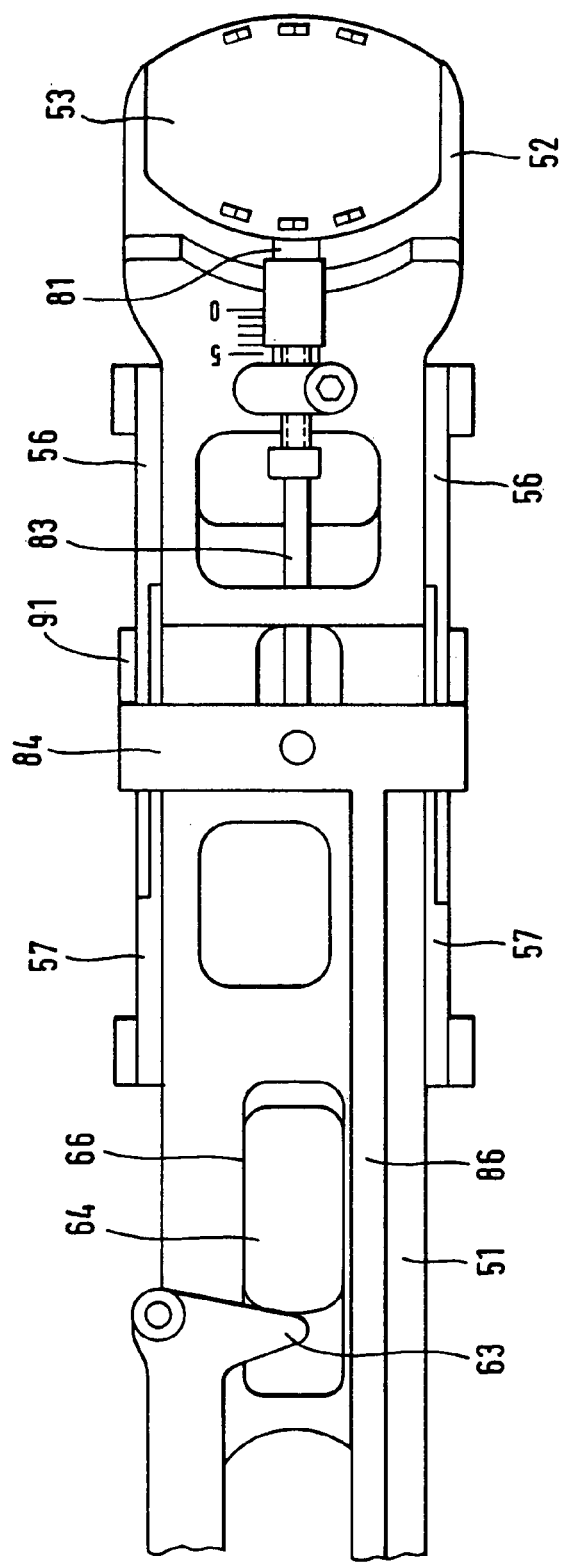
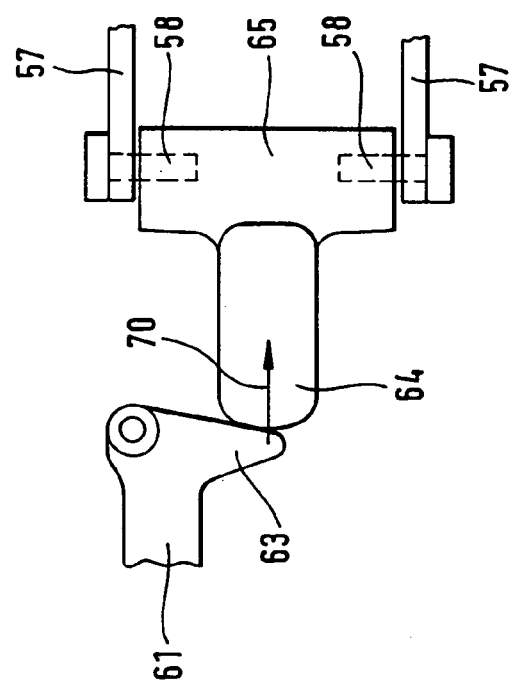
Fig.11
Fig.13

SURGICAL INSTRUMENT FOR INSERTING AN INTERVERTEBRAL ENDOPROSTHESIS

To insert an intervertebral endoprosthesis consisting of two prosthesis plates, each to be connected to a respective vertebra, and of a prosthesis core, an instrument is known (EP-B-333990) which has two fork-shaped prosthesis holders for the two plates. These guides are arranged on an expansion forceps with which it is possible first to insert only the approximated plates, without the prosthesis core, between two vertebrae, then to move them apart by expansion of the forceps, so that the prosthesis core can be inserted between the plates, and finally to move them towards each other again until they definitively enclose the prosthesis core. After the prosthesis has in this way reached its intended position, the instrument can be removed. The fork-shaped prosthesis holders are open at the end, so that the instrument can be easily removed.

However, when removing the instrument from the prosthesis, difficulties are sometimes occasioned by high frictional forces which may be caused by the instrument tilting or by the prosthesis holders becoming jammed on the vertebrae. There is then a danger that the prosthesis will be moved in an undesirable way as a result of this friction or as a result of abrupt movement of the instrument.

In an instrument of a different generic type (DE-U-200 12 549; U.S. Pat. No. 5,431,658), intended for inserting a one-piece implant between two vertebrae, it is known to push the implant in between a pair of guide rods by means of an advancing rod which has a vertebral limit stop. When the implant has reached the intended depth in the intervertebral space, this limit stop bears against one of the vertebrae, by which means the instrument is withdrawn from the vertebrae and the prosthesis upon further advance movement. This solution cannot readily be used on those instruments (DE-U-299 16 078) in which, as in the generic type according to the invention, two holders are provided for prosthesis plates which have to be spread apart for inserting a prosthesis core.

The invention is based on the object of making it easier to remove the instrument mentioned at the outset. This object is achieved by the features of claim 1.

Accordingly, a withdrawal device is provided for withdrawing the instrument from the prosthesis plates located in the prosthesis holders and/or from at least one of the adjacent vertebrae. Arranged on each prosthesis holder there is a slide which has a prosthesis limit stop and/or a vertebral limit stop and is displaceable in a slide guide between a retracted end position and an advanced end position. This is done using an actuating device which has a spacing-independent device for coupling the movement of both slides.

The slide bearing the prosthesis limit stop or vertebral limit stop is preferably movable on the instrument in a slide guide which is parallel to the guide direction of the prosthesis holder. In this guide, it can adopt a rear end position in which the prosthesis is held completely by the prosthesis holder.

The slide is situated in this end position until the prosthesis has reached the implantation position intended for it. In the front end position of the slide, the prosthesis limit stop or vertebral limit stop is advanced so far that the prosthesis is no longer held by the prosthesis holder and the instrument can be removed without difficulty. When the prosthesis has been fitted and the withdrawal device actuated, the instrument is moved back on the path of the slide bearing on the prosthesis or on the vertebra in relation to these parts, i.e. withdrawn from them.

This withdrawal requires a certain force application. For this reason, a transmission device is expediently arranged between the withdrawal device and a handle provided for actuating the latter. This transmission device can be formed, for example, by a threaded spindle which at one end acts on the slide and at the other end has a control knob to be actuated by the physician. In a preferred embodiment, the transmission device is formed by a lever device.

The handle and the transmission can be arranged permanently on the instrument. However, to make the instrument easier to use and to ensure that the view during the insertion procedure is not obstructed by unnecessary parts, it may be expedient for the handle (if appropriate together with the transmission device) to be provided separately from the instrument and for these parts to be designed in such a way that they can be easily connected to the instrument when said instrument is in the operating position. For example, the handle and the transmission device are formed by a forceps. On one of its short levers (the working lever), the forceps has coupling means which are designed to complement coupling means on the instrument. The other working lever of the forceps comes into engagement with the slide or slides when the forceps is connected to the instrument.

During withdrawal, the withdrawal force should act on each of the two slides to ensure that one prosthesis plate is not subjected to greater loading than the other one. This applies regardless of the mutual spacing of the plates. In order to permit this, the invention provides for a rocker to be arranged between the withdrawal device and the parts of the slide interacting with the latter, the withdrawal force being transmitted substantially in equal parts to both slides via the pivot point of said rocker.

In another embodiment of the invention, the actuating device is securely connected to the instrument, and specifically to an instrument body which is securely connected to only one of the two prosthesis holders. Accordingly, the actuating device also acts directly only on this one slide. For synchronous driving of the other slide, a driver part is connected in terms of movement to the directly driven slide and engages with a driven part of the other slide via a spacing-independent coupling. This is preferably done by means of a limit stop which is connected to the directly driven slide and which is guided with it in the withdrawal direction and, independently of the mutual spacing of the prosthesis guides, reaches into the area of movement of another limit stop connected to the other slide. Other solutions are also conceivable, however. For example, the directly driven slide can have a toothed rack whose movement drives a pinion which is securely connected to a splined shaft which, in the area of the other slide, has a pinion which is axially displaceable thereon and which transmits its movement to a toothed rack connected to the other slide.

A particularly straightforward and easy-to-use instrument is obtained if the actuating device is not designed to be removable but instead is integrated for example as a push rod in the instrument body, in which case a grip can be connected to the end of the pusher rod and be moved in the longitudinal direction of the appliance.

If combined vertebral and prosthesis limit stops are provided, these can be used to determine the position of the prosthesis between the vertebrae, by inserting the instrument until the vertebral limit stop or the vertebral limit stops bear(s) on the vertebra or vertebrae. The prosthesis then has the position between the vertebrae which is determined by the depth spacing between the vertebral and prosthesis limit stops. In order to be able to insert the prosthesis to a different depth in the ventral-dorsal direction and take account of different anatomical relationships, this depth spacing can expediently be modified. This can be done, for example, by making available different slides which have a different depth spacing between the vertebral and prosthesis limit stops and which are inserted into the instrument as selected. Alternatively, the slide is permanently secured to one of the two limit stops, while the other limit stop is available in different formats or can be connected to the slide in different locking positions. An embodiment is preferred in which an adjustment device is provided which is designed for changing the spacing between the prosthesis limit stop and the vertebral limit stop. It is preferably arranged on the slide and has a slide guide with threaded spindle for one of the two limit stops. It is possible to determine pre-operatively, by evaluation of X-ray images, or intra-operatively, by taking measurements, how great the depth spacing between the prosthesis and the contact margin of the vertebra should be. Based on this value, the depth spacing between the vertebral and prosthesis limit stops of the instrument is then adjusted using the adjustment device. For this purpose, it is expediently provided with an adjustment scale. Inserting the instrument until its vertebral limit stops or its vertebral limit stop reach(es) the contact margin of the associated vertebra or vertebrae ensures that the prosthesis is positioned at the desired depth.

Figure 2:
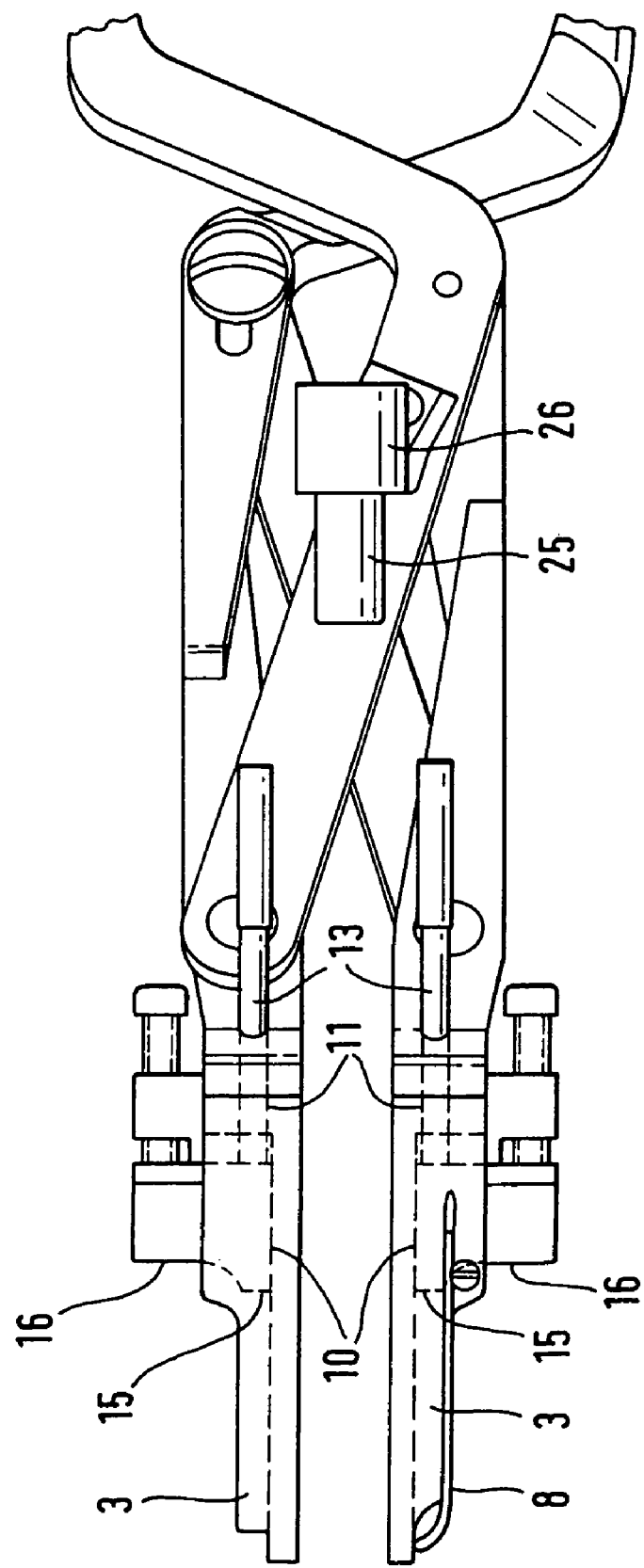
Figure 3:
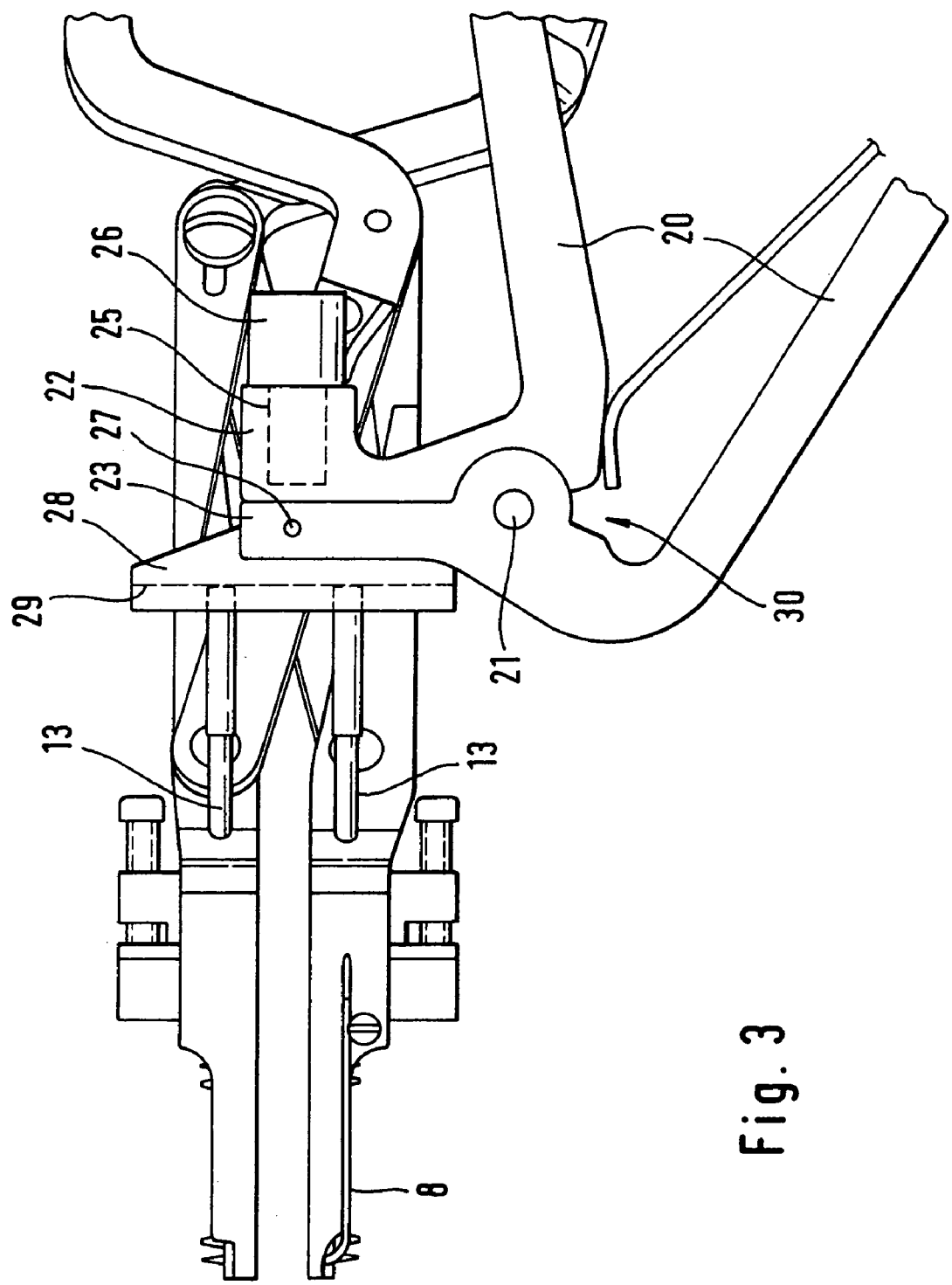
Figure 4:
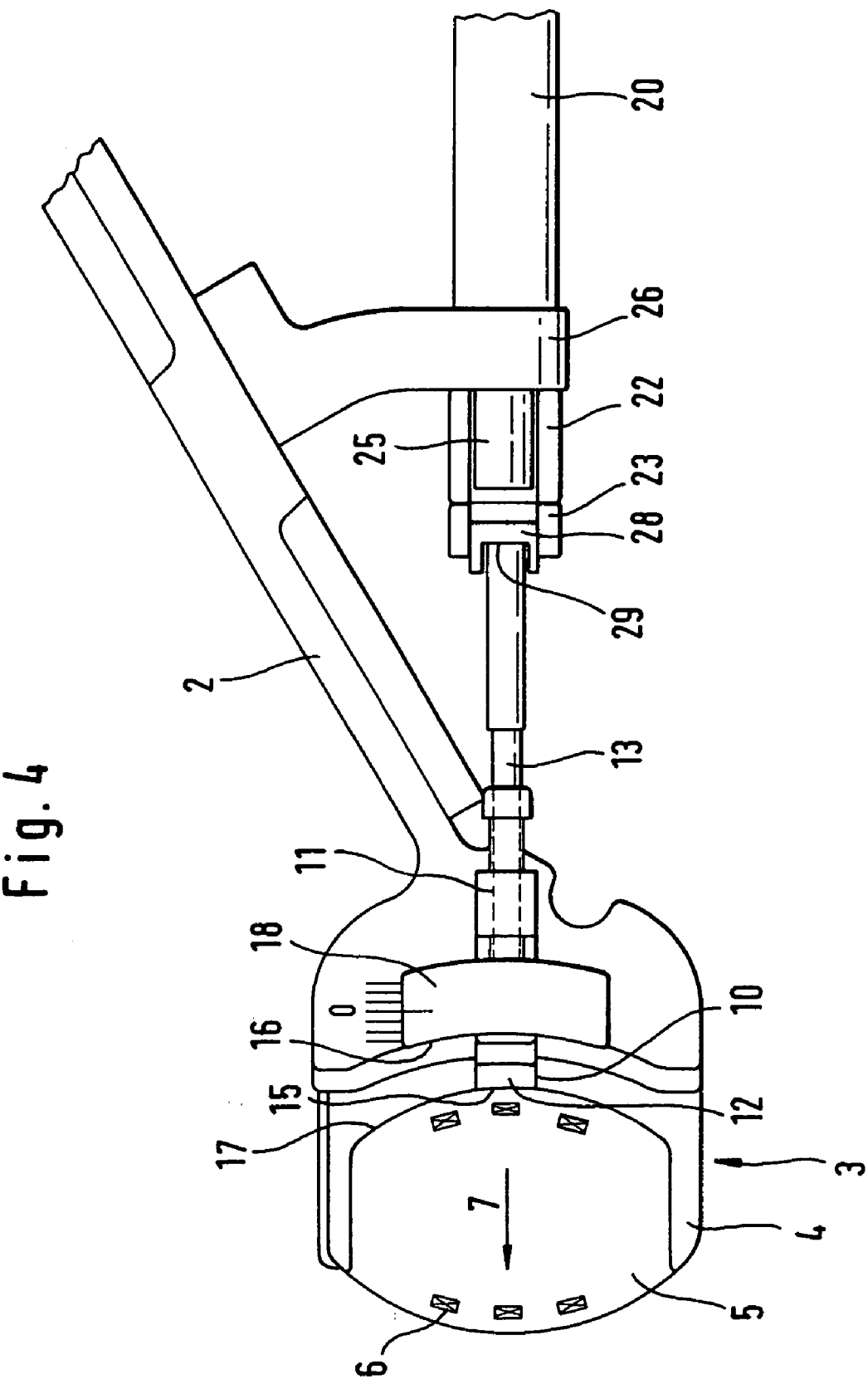
Figure 5:
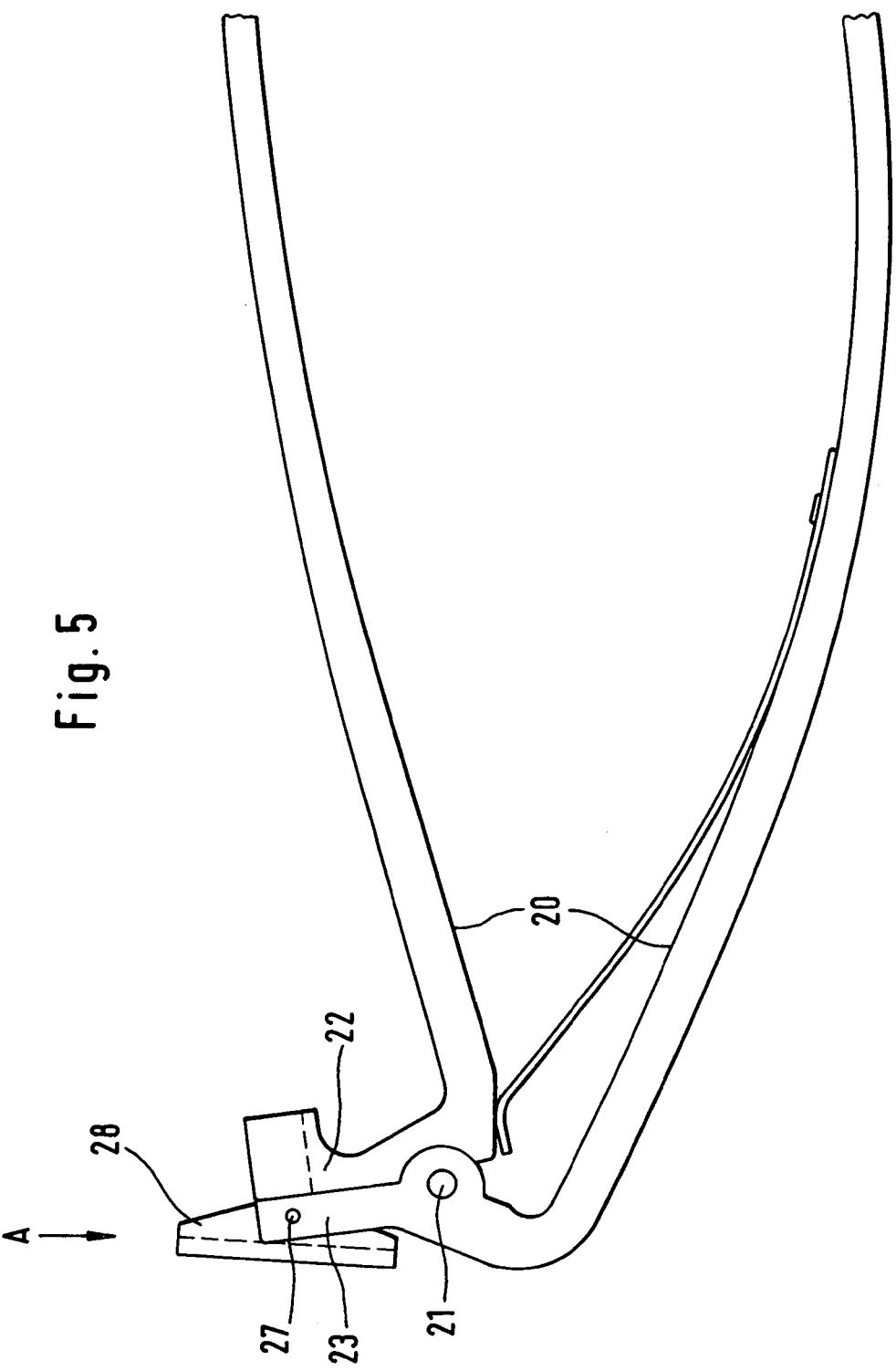
Figure 8:
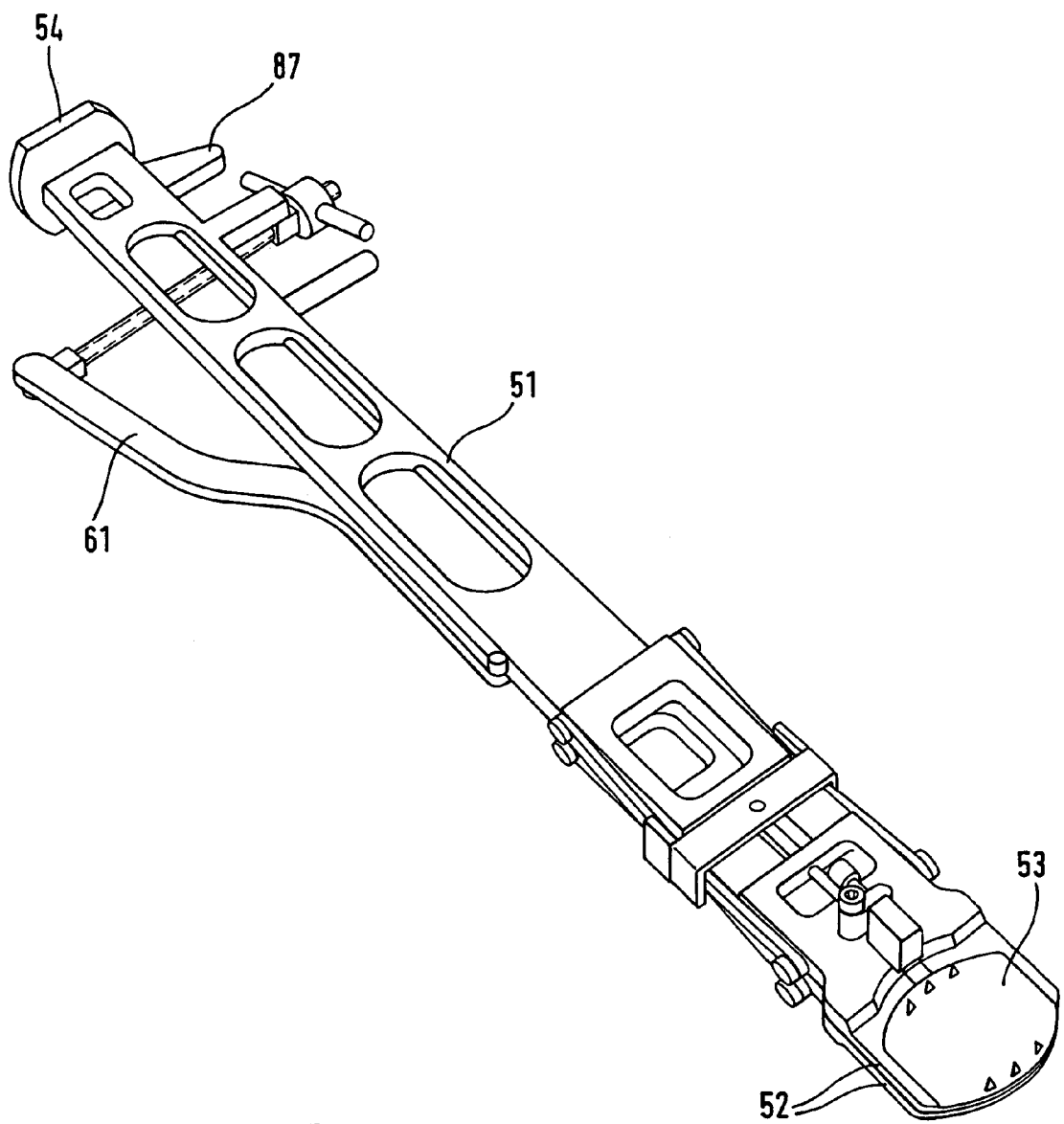
Figure 9:
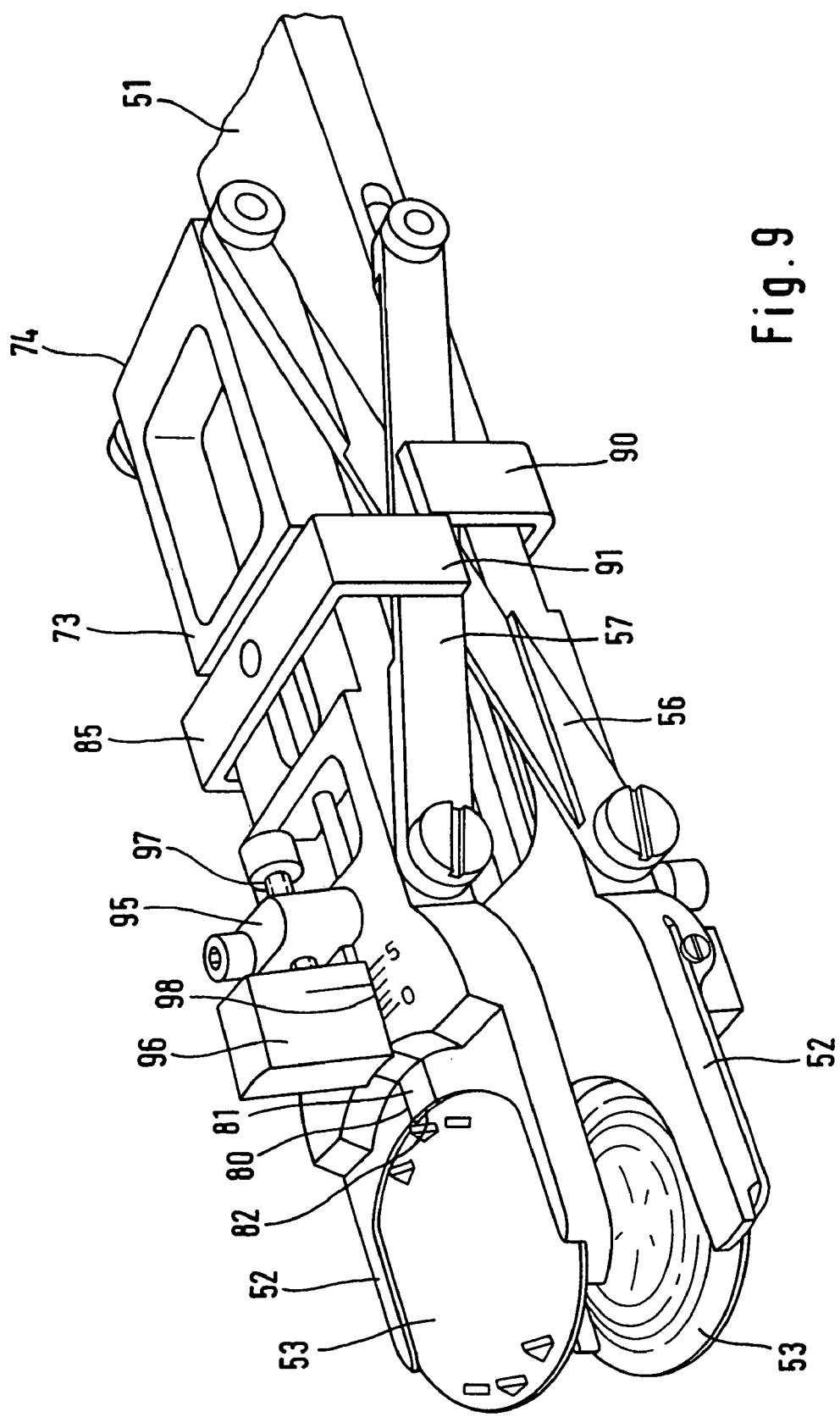
Figure 10:
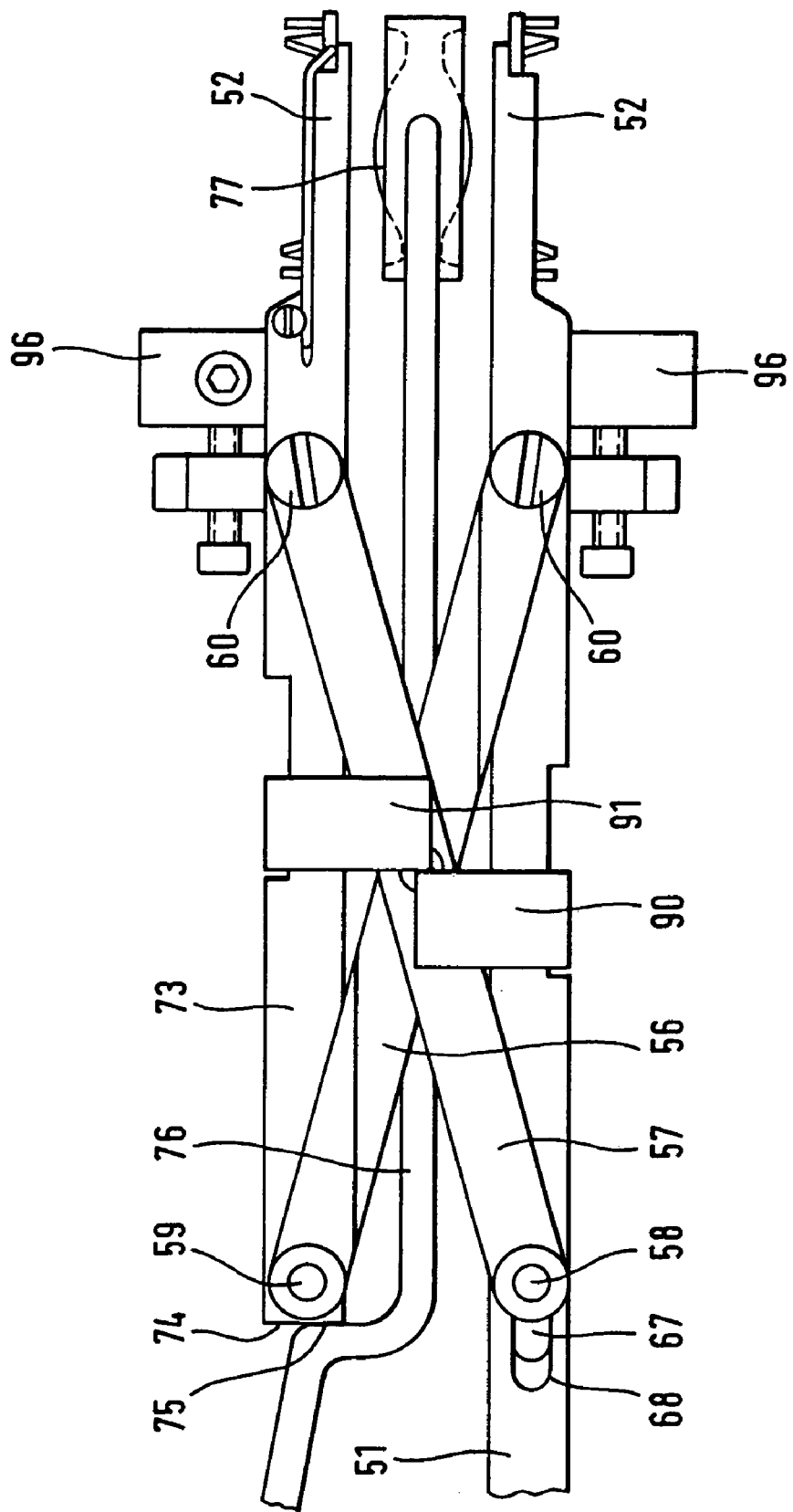
Figure 12:
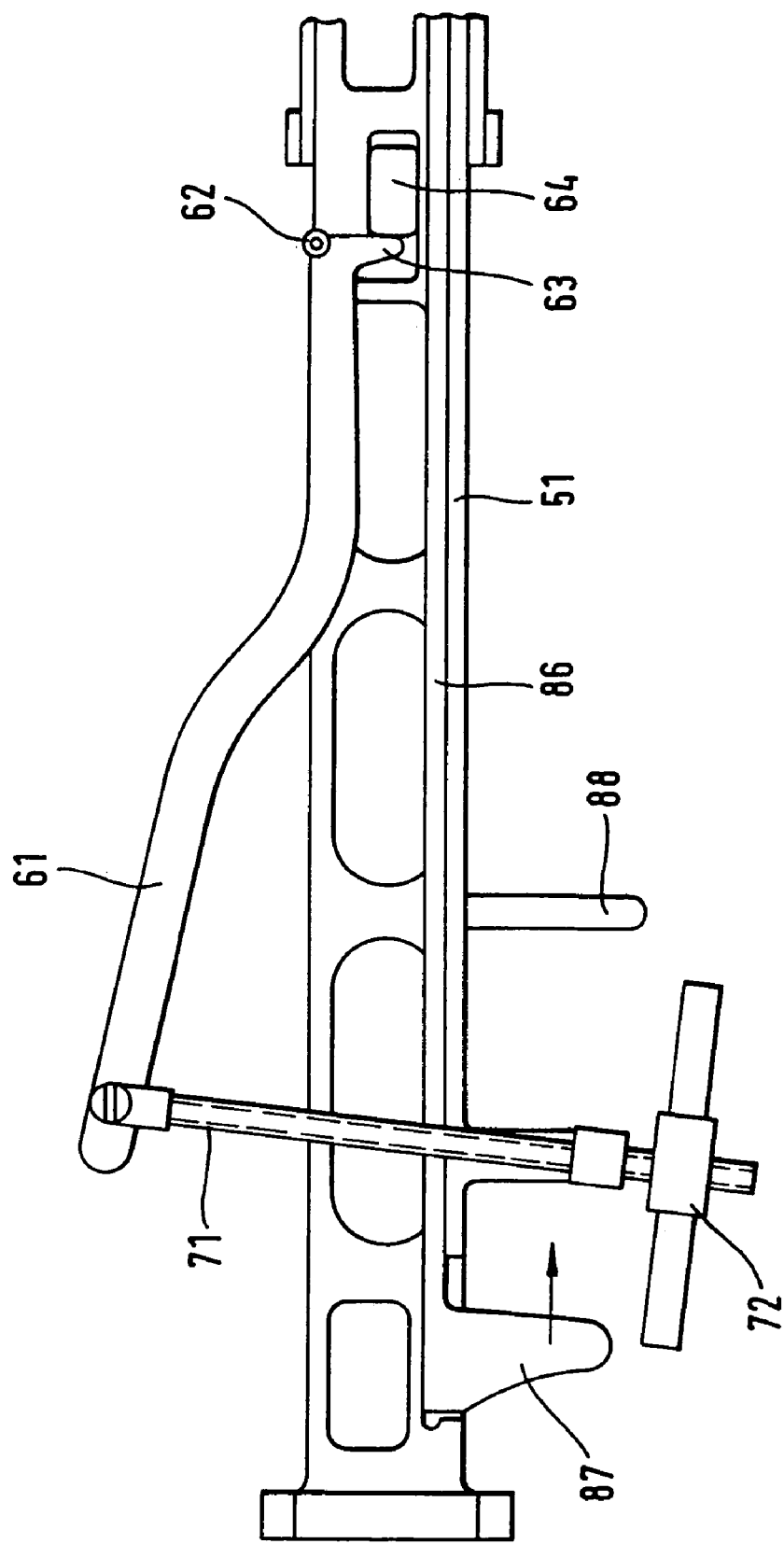

The invention is explained in greater detail below with reference to the drawing which depicts an advantageous illustrative embodiment. In said drawing:

FIG. 1 shows an overall view of the instrument,

FIG. 2 shows a view of the front section of the instrument, on an enlarged scale, FIG. 3 shows a view corresponding to FIG. 2, with withdrawal forceps applied, FIG. 4 shows a view corresponding to FIG. 3, seen in a vertical direction, FIG. 5 shows the withdrawal forceps, FIG. 6 shows a partial view of the withdrawal forceps, seen from the direction A in FIG. 5, FIG. 7 shows a detail of the slide, FIG. 8 shows the overall view of a second instrument, FIG. 9 shows a perspective view of the front section of this instrument, FIG. 10 shows a side view of the front section, FIG. 11 shows a bottom view of the front section, FIG. 12 shows a bottom view of the rear section, and FIG. 13 shows a detail of the actuating device.

The instrument shown in FIGS. 1 to 7 is an expansion forceps with hand levers 1 and with working clamps 2 which are guided in parallel and each have a prosthesis holder 3 at their front ends. As can best be seen from FIG. 4, the prosthesis holders 3 are designed in a U-shape with two side branches 4. They each receive the side edges of a respective prosthesis plate 5 in slide grooves. The view in FIG. 4 is directed towards the outside of a prosthesis plate 5 which is intended to bear on a vertebral body and has teeth 6 for better connection thereto. The prosthesis holder is designed in such a way that the prosthesis can be removed in arrow direction 7 with sufficient ease. It is secured against inadvertent release by means of a spring 8. For details of the design and use, reference may be made to EP-B-333990.

Behind the space intended for receiving the prosthesis, the prosthesis holder 3 forms a central guide groove 10 which is arranged in the same direction and to which a bore 11 is contiguous towards the rear in the same direction. The groove 10 receives a slide 12 which can slide easily therein in the groove direction but which is guided securely and connected to a rod 13 which is guided through the bore 11 and rearward from the latter. The slide 12 can be displaced in the longitudinal direction in the groove 10, as can be seen from the different adjustment of the lower and upper slides in FIG. 2.

The slide 12 forms a prosthesis limit stop 15 and a vertebral limit stop 16 which, in relation to the latter, is set back slightly, which limit stops are connected securely to one another in the example shown. In the rear end position of the slide, the prosthesis limit stop 15 lies flush with the rear edge 17 of the space provided for receiving the prosthesis 5. The instrument is introduced into the intervertebral space until the vertebral limit stop bears on the ventral margin of the vertebra in question. The spacing between the limit stops 15 and 16 thus determines the depth of insertion of the prosthesis. If the part 18 forming the vertebral limit stop 16 is made displaceable on the slide 12, the depth of insertion of the prosthesis can be predetermined variably. The enlarged view in FIG. 7 shows a slide 12 on which the vertebral limit stop 16 is formed by a separate block 19 which can be displaced in relation to the prosthesis limit stop 15 by means of a threaded spindle 31. For easier adjustment and control of the spacing between prosthesis limit stop 15 and vertebral limit stop 16, an adjustment scale 32 is provided on the slide 12. In the example shown, it cooperates with a rear edge of the vertebral limit stop 16 acting as indicator. Scale and indicator can also be arranged in another way, for example the marking on a side face of the vertebral limit stop 16 and the scale on an upper face of the prosthesis guide 3.

It can be clearly seen from the view in FIG. 4 that the prosthesis limit stop pushes the prosthesis out of the prosthesis holder when the slide is advanced. When the prosthesis is fixed between two vertebrae, the instrument is thereby withdrawn from the prosthesis. To do this (see FIGS. 2 and 3), the rods 13 must be pushed forwards in relation to the instrument. This is done using the withdrawal forceps shown in FIG. 5, which forceps can be easily connected to the instrument. Its grip branches 20 spread apart via a spring merge into working levers 22, 23 beyond the hinge point 21, which working levers 22, 23 extend substantially transverse to the direction of the grip branches 20. The working lever 22 includes a receiving opening 24 which is demarcated in a U-shape and whose width is slightly greater than the diameter of a pin 25 which on a bracket 26 which is arranged on the instrument in such a way that it is arranged approximately centrally in relation to the rods 13 independently of the respective spreading of the prosthesis holders 3.

Arranged on the front working lever 23 there is a rocker 28 which can pivot about an axis 27. The pivot point 27 lies approximately in the direction of the centre axis of the pin 25 when the withdrawal forceps is applied to the instrument (FIG. 3). The side of the rocker 28 directed away from the pin 25 includes a groove 29 whose width is slightly greater than the diameter of the rods 13 at their rear ends. When the expansion forceps is applied to the instrument in the direction of arrow 30 (FIG. 3), so that the pin 25 can be received by the opening 24, the rear ends of the rods 13 slide into the groove 29 and then lie at approximately the same distance either side of the pivot point 27 of the rocker 28. If the grip branches 20 of the withdrawal forceps are now pressed together, the working lever 23 moves forwards in relation to the bracket 26 supporting the working lever 22, so that the rods 13 and thus the slides 12 are moved forwards via the rocker 28. In this way, the prosthesis plates situated in the prosthesis holder are pushed forwards out of the guide or, to put it another way, the instrument is withdrawn from the prosthesis. Part of the withdrawal force is also transmitted to the vertebrae via the vertebral limit stops 16. If this is not desirable, the vertebral limit stops 16 can be set back slightly by means of the adjustment device after the prosthesis has been positioned and immediately before the instrument is withdrawn, so that said vertebral limit stops 16 no longer bear on the vertebrae. The vertebrae then remain free from forces during withdrawal.

FIGS. 8 to 12 show an alternative embodiment. At the front end of the instrument body 51 there are two holders 52 for prosthesis plates 53. The prosthesis holders 52 are fork-shaped and open at the end. Their side branches form guides for the edge of the prosthesis plates 53. They make it possible, by overcoming a frictional force, to insert the prosthesis plates into the prosthesis holders 52, and remove them from said prosthesis holders 52, in the longitudinal direction of the instrument. At the rear end, the prosthesis body 51 has a strike plate 54. By striking this plate, the prosthesis plates 53 held by the prosthesis holders 52 can be driven between two vertebrae.

The lower of the prosthesis holders 52 (FIGS. 9 and 10) is securely connected to the instrument body 51 and, in the example shown, even made integral therewith. The upper prosthesis holder 52 is connected to the instrument body 51 via a scissor arrangement consisting of scissor members 56, 57. The scissor arrangement 56, 57 is designed in such a way that the upper prosthesis holder 52 can move exclusively perpendicular to the lower prosthesis holder 52 and parallel to it. The prosthesis holders can be brought as close as possible to one another (FIG. 1) so that it is easier to drive them into the intervertebral space. They can be spread apart together with the adjoining vertebrae (FIGS. 9 and 10) in order to create space for introducing the prosthesis core between the prosthesis plates 53. They are then brought back towards each other in order to secure the prosthesis core in the desired position. The instrument can then be removed.

The rear pins 58, 59 of the scissor members 56, 57 slide in oblong holes in the instrument body 51, their direction corresponding to the longitudinal direction of the instrument, whereas the front pins 60 are connected rigidly to the prosthesis holders 52. In order to spread the prosthesis holders, a device is provided which moves the rear pin 58 of the scissor member 57 in the longitudinal direction of the instrument. It is for this purpose that the grip lever 61 is provided which can pivot on the instrument body about an axis 62 and has a working lever 63 which acts on the rear end of a slide block 64 which is part of a T-shaped carriage 65 (FIG. 13) on whose crosshead the rear pins 58 of the scissor members 57, arranged on both sides, are articulated. The carriage 65 is guided in the longitudinal direction of the instrument body. It will be seen from FIG. 11 that the parallel edges of the slide block 64 are guided between correspondingly parallel edges 66 of a cut-out in the instrument body. It can be seen from FIG. 10 that the ends 67 of the crosshead are guided in oblong holes 68. When the grip lever 61 is applied to the instrument body upon pressing-together of the levers of a forceps, its working lever 63 presses the carriage 64 in the direction of arrow 70 (FIG. 13). In this way, the rear end of the scissor member 57 is driven forwards, as a result of which the prosthesis holders 52 are spread apart. The working lever 63, the carriage 65 and the oblique connectors 57 thus form an arrangement for adjusting the spacing of the prosthesis holders 52. It will be appreciated that this arrangement can also be replaced by other embodiments. It will further be seen that the spreading force does not necessarily have to be exerted via the oblique connectors 57. If the angle between the oblique connector 57 and the longitudinal direction of the instrument is too small for exerting a substantial spreading force, a separate member can be provided for the spreading.

Upon spreading of the prosthesis holders, considerable forces occur. For this reason, the hand lever 61 is supplemented with a threaded spindle 71 with a butterfly nut 72, which makes the procedure easier and makes it possible to temporarily hold the instrument in the spread position.

In this position, a channel-like free space is formed between the instrument body 51 and the plate 53 continuing the upper prosthesis holder 52 rearwards, on the one hand, and between the lateral scissor arrangements 56, 57 on the other hand. Using an instrument 76, the prosthesis core 77 can be guided through this free space between the prosthesis plates 52 (FIG. 10). The instrument 76 has a limit stop 75 which bears on the rear edge 74 of the plate 73 when the prosthesis core 77 has exactly reached the intended position between the prosthesis plates 52.

The device for ejecting the prosthesis plates 53 from the prosthesis holders 52 or for withdrawing the instrument from the prosthesis holders or the adjoining vertebrae will now be described. The prosthesis holders 52 include, behind the space for receiving the prosthesis plates 53, a guide groove 80 which extends in the longitudinal direction of the instrument and thus in the direction of sliding of the prosthesis holders 52. It includes a slide 81 whose front end 82 strikes against the edge of the prosthesis plate located in the prosthesis holder and is for this reason referred to as a prosthesis limit stop. The rear end of the slide 81, not visible in FIGS. 9 and 11, is rigidly connected to a rod 83 which is likewise guided in the longitudinal direction of the instrument. As is shown in FIG. 11, the rear end of the rod 83 mounted in the instrument body 51 is secured on a limit stop element 84, the nature of which will be explained below. It is likewise displaceable in the longitudinal direction of the instrument. The limit stop element 84 is in turn rigidly connected to a push rod 86 which is mounted so as to be longitudinally displaceable in the instrument body 51 and (see FIG. 12) leads to a handle 87. When the operating surgeon pushes the handle 87 forwards in the direction of the arrow, the push rod 86, the limit stop element 84, the rod 83 and the slide 81 are pushed forwards, so as to push the prosthesis plate 53 out of the prosthesis holder 52. The hand of the operating surgeon can rest on a journal 88 (FIG. 12) which is connected securely to the instrument body 51.

The movement of the handle 87 acts directly only on the slide 81 which is arranged in the lower part of the instrument, namely in the instrument body. To ensure that the slides 81 of both prosthesis holders move in synchrony, a movement-transmitting device is provided. The rod 83 controlling the slide 81 of the upper prosthesis holder is securely connected at its rear end to a limit stop element 85 which, like the limit stop element 84 of the lower prosthesis holder, is guided movably in the longitudinal direction of the instrument. The lower limit stop element 84 has, on both sides, upwardly protruding limit stop branches 90 which lie behind and adjacent to the branches 91 which protrude downwards on both sides from the upper limit stop element 85. When the prosthesis plates 53 are located in their rearmost position in the prosthesis holders 52 and the prosthesis limit stops 82 touch them, the mutually adjacent end faces of the limit stop branches 90, 91 also bear on one another. If, by actuating the handle 87, the lower limit stop element 84 with the limit stop branches 90 is now pushed forwards, their cooperation with the limit stop branches 91 of the upper limit stop element means that the slide 81 of the upper prosthesis holder is pushed forwards too. The two slides 81 thus move in synchrony. Since the interacting limit stop surfaces 90, 91 are perpendicular to the longitudinal direction of the instrument, the synchronous movement of the slides 81 is guaranteed independently of the respective spacing of the prosthesis holders from each other.

Each slide 81 has an attachment 95 rigidly connected to it, and a block 96 which is guided in the longitudinal direction of the slide and whose end face forms the vertebral limit stop. If the prosthesis holders with the prosthesis plates 53 located therein are driven into the space between two vertebrae, the end faces of the vertebral limit stops 96 finally bear on the ventral margins of the vertebral bodies. The spacing of the end faces of the vertebral limit stops 96 from the prosthesis plates thus defines the depth at which the prosthesis plates arrive in the intervertebral space. This depth can be changed by adjusting the vertebral limit stops 96 on the slides 81. This is done by means of a threaded spindle 97 which is guided in a threaded bore of the attachment 95 and whose end is connected to the vertebral limit stop 96 in such a way as to be rotatable, but fixed in the longitudinal direction. By turning the threaded spindle 97, the operating surgeon can thus determine in advance the depth of insertion of the prosthesis plates 53 in relation to the ventral margin of the associated vertebra. A scale 98 helps him do this.

The invention claimed is:

1. Surgical instrument for inserting an intervertebral endoprosthesis which consists of two prosthesis plates and of a prosthesis core enclosed by these plates, said instrument comprising:
   two prosthesis holders which are open at the ends and can be spread apart from each other;
   a withdrawal device for withdrawing the instrument from the prosthesis plates located in the prosthesis holders and/or from at least one of the adjacent vertebrae, said withdrawal device having, on each prosthesis holder, a slide which has a variable vertebral limit stop;
   a slide guide in which said slide is displaced between a retracted end position and an advanced end position; and
   an actuating device which has a spacing-independent device for coupling the movement of both the slides;
   a device for transmitting a driving force between the withdrawal device and a handle formed by a lever arrangement;
   wherein the handle can be easily connected to the instrument when the transmission device is situated in the orerating position;
   wherein the handle and the transmission device are formed by a forceps configuration, and the forceps, on one of its working levers, and the instrument have complementary coupling means, while the other working lever acts on the slide;
   wherein a rocker is arranged between the withdrawal device and parts of the slide which interact with it, the rocker being a spacing-independent device for coupling their movement.

2. The surgical instrument according to claim 1, characterized in that the actuating device is arranged on an instrument body which is securely connected only to one of the two prosthesis holders, and the slide of this prosthesis holder is connected in terms of movement to a driver part which engages with a driven part of the other slide via a spacing-independent coupling.

3. The surgical instrument according to claim 2, characterized in that a driver part and the driven part are designed as limit stops guided in the withdrawal direction.

4. The surgical instrument according to claim 3, characterized in that the instrument body securely connected to one of the prosthesis holders includes a push rod with grip, which rod is connected in terms of movement to the associated slide.

5. The surgical instrument according to claim 2, wherein the instrument body is securely connected to one of the prosthesis holders, the prosthesis holder including a push rod with grip, the push rod is moveably connected to the associated slide.

6. The surgical instrument according to claim 5, characterized in that at least one slide has a prosthesis limit stop, wherein the spacing between these limit stops in the depth direction can be changed.

7. The surgical instrument according to claim 1, wherein at least one slide further comprises a prosthesis limit stop wherein the spacing between these limit stops in the depth direction can be changed.

8. The surgical instrument according to claim 7, further comprising an adjustment device for changing the spacing between the prosthesis limit stop and the vertebral limit stop.

9. The surgical instrument according to claim 8, wherein the adjustment device is arranged on the slide, the adjustment device further comprising a slide guide with threaded spindle for one of the two limit stops.

10. The surgical instrument according to claim 9, characterized in that the adjustment device has an adjustment scale.

11. The surgical instrument according to claim 8, wherein the adjustment device further comprising adjustment scale.

12. The surgical instrument according to claim 11, characterized in that a kinematic connections between the instrument parts bearing the two prosthesis holders are arranged outside a central through-opening which extends in the instrument direction and whose width corresponds at least to the width of the prosthesis core and of an insertion instrument for the latter.

13. The surgical instrument according to claim 1, further comprising a kinematic connections between instrument parts bearing the two prosthesis holders are arranged outside a central through-opening which extends in the instrument direction and whose width corresponds at least to the width of the prosthesis core and of an insertion instrument for the latter.

14. The surgical instrument according to claim 1, characterized in that a prosthesis limit stop on each vertebral limit stop is independent.

* * * * *